United States Patent [19]
Jung et al.

[11] Patent Number: 5,231,013
[45] Date of Patent: Jul. 27, 1993

[54] POLYCYCLIC PEPTIDE ANTIBIOTIC GALLIDERMIN

[76] Inventors: Gunther Jung, Ob der Grafenhalde 6, D-7400 Tubingen; Roland Kellner, Dr. H. Winter Strasse 17, D-6148 Heppenheim; Hans Zahner, Im Hopfengarten 13, D-7400 Tubingen; Friedrich Gotz, Beim Herbstenhof 31, D-7400 Tubingen; Thomas Horner, Quenstedterstrasse 34, D-7400 Tubingen; Rolf G. Werner, Hugo-Haring-Strasse 72, D-7950 Biberach; Hermann Allgaier, Mozartstrasse 30, D-7951 Mittelbiberach, all of Fed. Rep. of Germany

[21] Appl. No.: 353,719

[22] Filed: May 18, 1989

[30] Foreign Application Priority Data

May 18, 1988 [GB] United Kingdom ............... 8811760

[51] Int. Cl.⁵ .................. C12P 21/04; C12N 1/20

[52] U.S. Cl. ..................... 435/71.3; 435/252.1; 435/882

[58] Field of Search ............. 435/71.3, 252.1, 882

[56] References Cited

PUBLICATIONS

Kellner et al., "Gallidermin A New Lanthionine-Containing Polypeptide Antibiotic", European J. Biochem, 177 (1), 1988, pp. 53–60.
Fielder et al., Chromatographia, vol.26 (1988) pp. 215–220.
Devriese et al., J. of Systematic Bacteriology, vol. 33, No. 3, (Jul. 1983), pp. 480–486.

*Primary Examiner*—Douglas W. Robinson
*Assistant Examiner*—Susan M. Weber
*Attorney, Agent, or Firm*—D. E. Frankhouser; M-E. M. Timbers; A. R. Stempel

[57] ABSTRACT

A new polycyclic peptide antibiotic termed gallidermin is disclosed and described, together with a process for producing such antibiotic by fermination of a new microorganism, *Staphylococcus gallinarum* (DSM 4616).

3 Claims, 6 Drawing Sheets

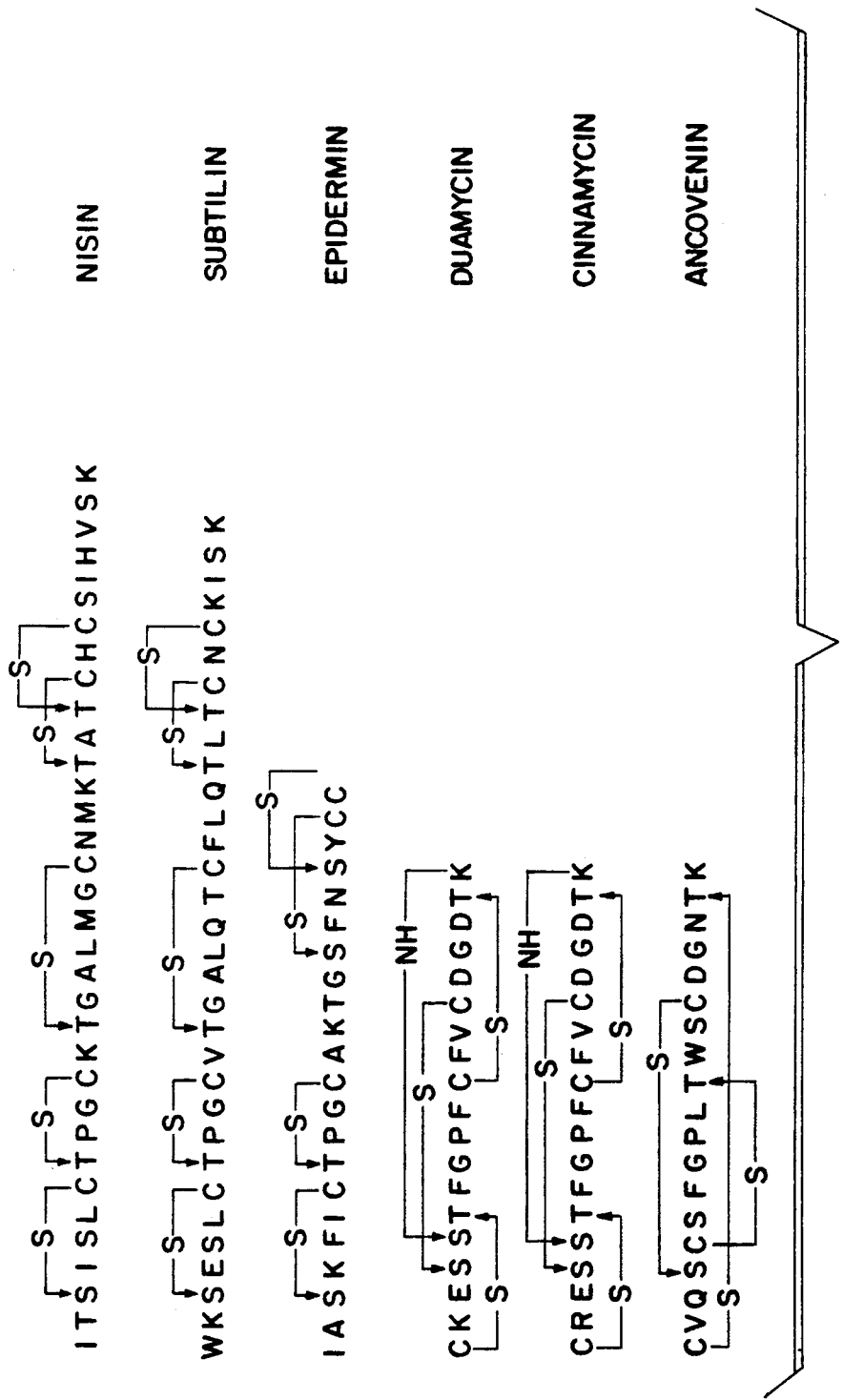

POLYCYCLIC PEPTIDE ANTIBIOTIC GALLIDERMIN

The present invention relates to a novel antibiotic, named Gallidermin, salts thereof, pharmaceutical compositions containing the same and to methods for the production thereof.

THE INVENTION

Figure 1:
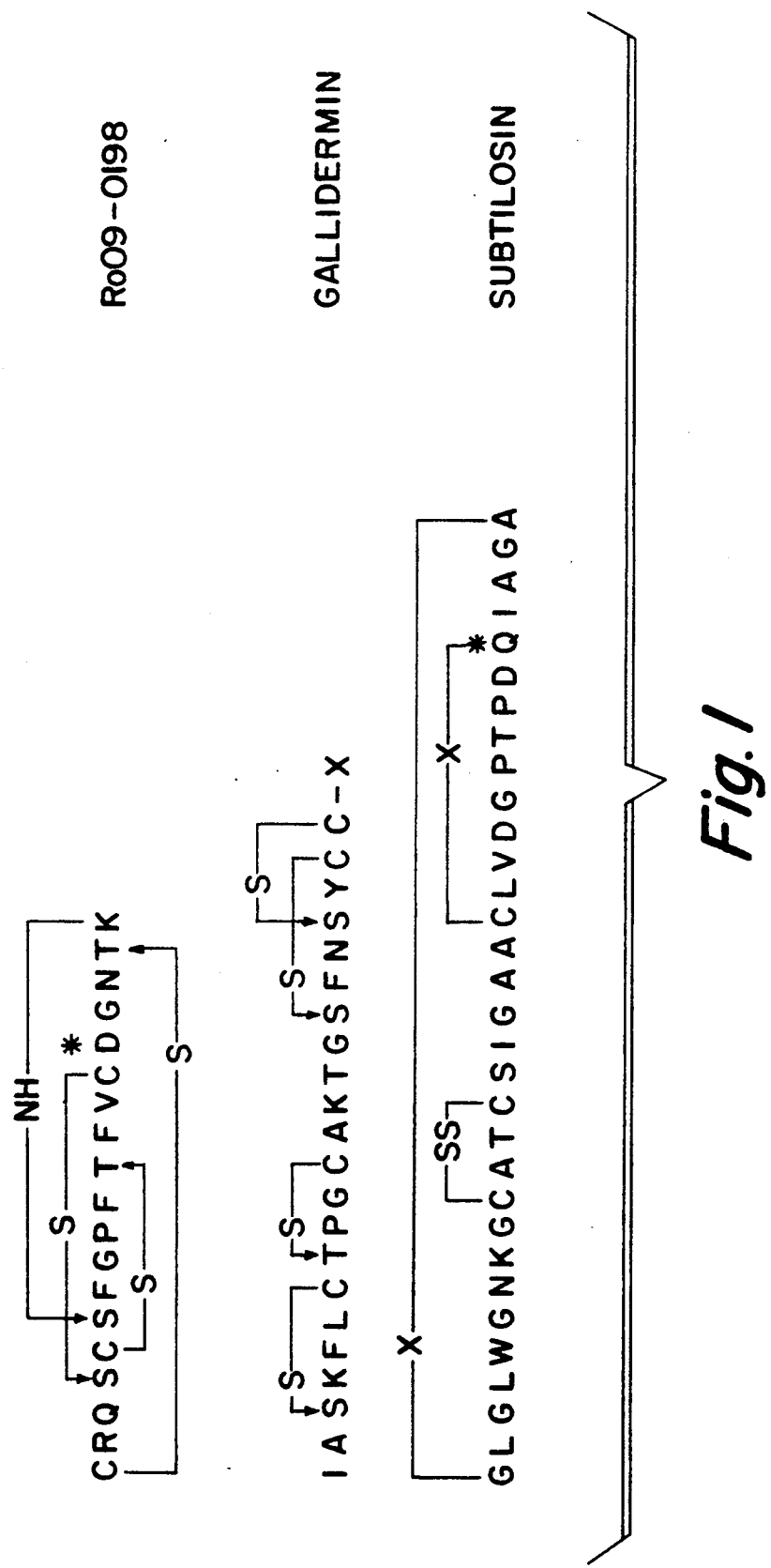
FIG. 1 shows peptide sequences of various peptide antibiotics.

A number of polycyclic peptide antibiotics are known. Some of these antibiotics contain a lanthionine structure, for example nisin, subtilin, duramycin, cinnamycin, ancovenin, Ro 09-0198, pep5 and epidermin.

Typically these antibiotics possess a high content of unsaturated amino acids (dehydroalanine, dehydrobutyrine) and thioether amino acids (meso-lanthionine, (2S, 3S, 6R)-3-methyllanthionine. Lysinolanine, 3-hydroxyaspartic acid and S-(2-aminovinyl)-D-cysteine were also found in some members.

Apart from structural similarities between duramycin and cinnamycin little sequence homology appears to exist between these various known peptide antibiotics. This is rendered clear in FIG. I which shows the propeptide sequences of the antibiotics. From this Figure it will be clearly apparent, for instance, that epidermin shows no significant sequence homology with the other antibiotics.

It may, moreover, be noted that the provenance of epidermin differs from that of the other antibiotics (apart from pep5) in that it is obtained by cultivating a strain of the microorganism *Staphylococcus epidermis* whereas the other antibiotics have been obtained by cultivation of strains of *Streptococcus lactis* (Nisin), *Bacillus subtilis* (subtilin) *Streptomyces cinnamoneus* and Streptomyces sp. (Cinnamycin, Duramycin and Ancovenin) and *Streptoverticillum griseoverticillum* (Ro 09-0198).

Epidermin is particularly active against the microorganism *Propionibacterium acnes* and for that reason has been studied as a possible therapeutically active substance for use in the treatment of infections due to this microorganism.

We have now found, however that a peptide closely related structurally to epidermin has a surprisingly greater activity towards *Propionibacterium acnes* compared to epidermin. In view of the fact that the known peptide antibiotics generally differ considerably, structurally, one from another it is unexpected that a further antibiotic exists which differs from one of their members by the replacement of merely one amino acid, and it is further surprising and entirely unpredictable, that such interchange of a single amino acid in epidermin would lead to a significant increase in activity against the microorganism *Propionibacterium acnes*.

The present invention, therefore, provides a new compound, which is named Gallidermin, having the structure

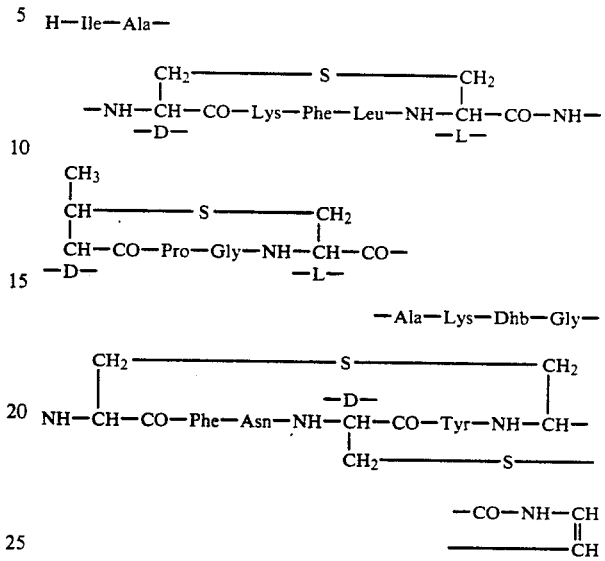

and the pharmaceutically acceptable acid addition salts thereof.

Gallidermin can be produced by cultivation of the microorganism *Staphylococcus gallinarum* (F16/P57) Tu 3928 or mutants thereof. The microorganism has been deposited with the Deutsche Sammlung von Microorganism (DSM) under the terms of the Budapest Treaty on May 18, 1988. The accession number is DSM 4616.

*Staphylococcus gallinarum* (F15/P57) Tu 3928 (DSM 4616) belongs to a newly discovered staphylococcus species which was described by Devriese et al. (Int. J. Syst. Bacteriol. 33, 480-486 (1983)). The strains can be isolated from chicken crests.

The strain *S. gallinarum* (F16/P57) Tu 3928 (DSM 4616) is described in detail in the article by Devriese et al. mentioned in the preceding paragraph.

It is to be noted that the DNA/DNA homology between *S. gallinarum* (F16/P57) Tu 3928 (DSM 4616) and *S. epidermis* is only between 10 and 25% indicating that the G and epidermin producing strains belong to clearly separate species. It is also to be noted that the two species are distinguished by several other markers such as the novobiocin resistance and the wide range of positive carbohydrate reaction (cellobiose, mannitol, melizitose, trehalose, arabinose, ribose and xylitol) of *S. gallinarum* (Arch. Microbiol. 92,65-85 (1973), J. Clin. Microbiol. I, 82-88, (1975), and the "Procaryotes", Springer Verlag, Heidelberg, 1548-1569 (1981).

The present invention accordingly further provides a process for the preparation of gallidermin and pharmaceutically acceptable salts thereof which comprises cultivating a microorganism capable of expressing gallidermin, preferable *S. gallinarum* (F16/P57) Tu 3928 (DSM 4616) under conditions whereby gallidermin is expressed and secreted in the culture medium, isolating the gallidermin from the culture medium, and, if desired, converting the isolated substance to a pharmaceutically acceptable salt thereof.

The cultivation of gallidermin producing microorganisms, such as *S. gallinarum* (F16/P57) Tu 3928 (DSM 4616) can be carried out according to standard methods using conventional culture medium. For instance *S. gallinarum* (F15/P57) Tu 3928(DSM 4616) can be cultivated in a medium containing suitable nitrogen source, carbon source, and a hydroxide of an alkaline earth metal, for instance a medium containing meat extract, Ca(OH)$_2$ in a suitable bioreactor. Cultivation should be under aeration and in the pH range of e.g. 5.4 to 8.5, preferably starting cultivation at a pH in the range of 6 to 7.

Gallidermin can be isolated from the fermentation broth in any suitable conventional manner used for isolating small molecular weight proteins from such media.

It has been found in particular that gallidermin may be readily isolated by the simple expedient of treating the culture medium with an adsorber followed by a procedure including the steps of adsorption on a weak cationic ion exchange resin, desalting and optionally a further chromatographic purification stage, e.g., reverse phase-HPLC or chromatography on Gel Sephadex LH20 using, e.g., methanol/0.01N HCl LH20 (9:1) a eluant.

As the compound gallidermin is strongly basic it will readily form acid addition salts with suitable, pharmaceutically acceptable acids according to conventional methods. Physiologically acceptable organic or inorganic acids which can be used for this purpose are, for example, hydrochloric acid, hydrobromic acid, sulphuric acid, benzosulphonic acid, methanesulphonic acid, p-toluenesulphonic acid and cyclohexylsulphamic acid.

Antibacterial Activity

Minimal inhibitory concentrations (MIC, Table 1) were determined in liquid BF medium of the following composition: sodium lactate 0.5%, sodium sulfate 0.5%, potassium dihydrogenphosphate 0.05%, dipotassium hydrogenphosphate 0.15%, magnesium chloride 0.02%, ammonium chloride 0.05%, glucose 1%; supplemented (per ml) with Ca-pantothenate 50 μg, folic acid 0.25 μg, niacin 50 μg, p-aminobenzoic acid 25 μg, pyridoxal hydrochloride 50 μg and riboflavin 25 μg.

The results are shown in Table 1 below.

TABLE 1

| Microorganisms | MIC (μg/ml) |
| --- | --- |
| St. aureus SG 511 | 4 |
| St. aureus E 88 | 8 |
| St. epidermidis ATCC 12228 | 4 |
| St. pneumoniae ATCC 6302 | 4 |
| Sc. pyogenes ATCC 8668 | 1 |
| Sc. faecalis ATCC 29212 | 64 |
| Cb. xerosis ATCC 9755 | 1 |
| E. coli ATCC 11775 | 128 |
| Ps. aeruginosa BC 19 | 128 |
| Mc. luteus ATCC 9341 | 0.25 |
| Mc. luteus 15957 | 0.5 |
| Bac. fragilis (Bonn) | 128 |
| Bac. fragilis (Koln) | 128 |
| Peptostreptococcus anaerobicus | 0.5 |

In a comparative study with epidermin or *Propionibacterium acnes* the following MIC values were obtained:

| | MIC (μg/ml) |
| --- | --- |
| Gallidermin | 0.125 |
| Epidermin | 0.25 |

In view of its broad spectrum of antibacterial activity, gallidermin and its acid addition salts are useful for combatting bacteria and for treating bacterial infections. In particular, in view of their activity against important strains of *Propionibacterium acnes*, gallidermin and its acid addition salts are particularly useful in combatting skin infections such as acne, eczema, impetigo and cellulitis.

Thus according to a further feature of the present invention there are provided pharmaceutical compositions containing, as active ingredient, gallidermin or a pharmaceutically acceptable acid addition salt thereof, in association with one or more inert pharmaceutical carriers and/or excipients.

For pharmaceutical administration, the said polypeptide may be incorporated into preparations in either liquid or solid forms using carriers and excipients conventionally employed in the pharmaceutical art, optionally in combination with further active ingredients. The preparation may, for example, be applied orally, parenterally, enterally or preferably topically. Preferred forms include, for example, solutions, emulsions, gels, sprays, lotions, ointments, creams or powders.

Advantageously the compositions may be formulated as dosage units, each unit being adapted to supply a fixed dose of active ingredient. The total daily dose may, of course, be varied depending on the subject treated and the complaint concerned.

According to a still further feature of the present invention there is provided a method for the treatment of a patient suffering from, or susceptible to, infection, which comprises administering to the said patient an effective amount of gallidermin or a pharmaceutically acceptable salt thereof.

Gallidermin and its acid addition salts may also be used as an additive in cosmetic formulations especially those containing collagen in which it would act as a stabilizer.

A cosmetic preparation according to the present invention will include gallidermin or an acid addition salt thereof in association with a suitable carrier and/or excipient preferably collagen and optionally other additives suitable for cosmetic preparations such as perfumes and coloring agents.

EXAMPLE 1

Fermentation

Deep frozen cultures of *S. gallinarum* were used to inoculate agar discs containing GA medium. After maintaining the inoculated discs for 12 hours at 37° C. the dics were transferred into Erlenmeyer flasks containing 100 ml of a culture medium consisting of 3.3% meat extract, 3.0% malt extract, 0.38% Ca(OH)$_2$ at pH 6.5.

The inoculated flasks were maintained on a rotary shaker (Type RC106, Infors AG Basel) at a speed of 160 rpm, and a temperature of 36° C. for 8 hours. 200 ml of the resulting preculture was used to inoculate a 20 liter capacity bioreactor fermentation vessel (Giovanola Freres, Monthey) equipped with an intensor system. The medium used was the same as previously described in the preceding paragraph but containing additionally 6% NaCl. The aeration and stirring rates were adjusted to 0.4 vol./vol./min and 900 rpm. The pO$_2$ decreased rapidly to less than 10% within the first 5 hours; after 10 hours it rose to 80% within the rest of the fermentation time. The pH decreased from 6.5 to 5.4 within the first 8 hours, then it rose to 8.5 within the rest of the fermentation time. The maximal cell density was reached after 24 hours with 8–9×10$^9$ cells per ml. The development of foam was diminished by repeated additions of Polyurax Polyol PPG2025 (BP Chemicals).

Isolation

After 34 hours of fermentation adsorber resin Amberlite XAD-1180 was added directly into the fermenter vessel. Three batches of adsorber (in amounts of 2%, 1% and 1% in relation to the volume of the fermentation broth) were added at intervals of 45 minutes. The resin was filtered off and washed with 30 liters water and methanol/0.01N HCl (9:1) and the active eluant (1.4 liters) was concentrated under reduced pressure to give a dry weight of 2.7 g.

The product was then redissolved in methanol/0.01N HCl (9:1) and applied to Amberlite IRC-50 (H+-form) at pH 5.5. The resin was then washed with water and eluted with 0.1N HCl.

The eluat containing gallidermin was then contacted with Amberlite XAD-1180 to effect desalting, the solution separated from the Amberlite and subjected to lyophilisation.

The lyophilised product was thereafter dissolved in water and chromatographed by reverse-phase HPLC. This stage is performed on the Waters system having two pumps 501, an autoinjector WISP 712 and a gradient programmer M680. As stationaly phases Nucleosil 10C18 or 5C18 (columns 4.6×250 mm and 8×250 mm) and HD-galliderminel RP-7s-300 (column 4×150 mm) are used. Elution is carried out using various gradients of acetonitrile/o.1% trifuoracetic acid in water. The resulting eluat containing gallidermin was collected an could be concentrated by evaporation and if desired taken up in water and lyophilised several times. The lypphised product resulting from the desalting step can be purified by gel chromatography as an alternative to RP-HPLC. In such an operation the lyophilisate is dissolved in methanol/0.01N HCC (9:1) and passed through a column using S. gallinarum (F 16/P57) Tu 3928 (DSM 4616)ephadex LH 20 as a stationary phase. The resulting eluat containing gallidermin is handled as described above.

The production of gallidermin by fermentation, as for example described above, can be followed using the standard test strain *Micrococcus luteus* ATCC 9341 on agar plates containing 10 ml of gallidermin agar consisting of peptin 10 g, lab lemco powder (Oxoid) 8 g, NaCl 3 g, Na$_2$HPO$_4$ 2 g, glucose 10 g, (separately sterilized), agar 20 g, H$_2$ (1 liter), pH 7.2–7.4.

The strain *S. gallinarum* can be stored at −18° C. in tubes in the following medium: lab lemco powder (Oxoid) 33 g, malt extract (Frankel+Ech) 30 g, CA(OH)$_2$ 3.7 g, glycerol 400 g, H$_2$O 1 liter at pH 6.0.

EXAMPLE 2

Tincture 100 g of tincture contains:

| Gallidermin | 1.0 g |
|---|---|
| Ethanol (94.5% by volume) | 56.0 g |
| 1,2-Propylene glycol | 40.0 g |
| Demineralized water | 3.0 g |

Preparation

Gallidermin is dissolved in a mixture of ethanol/1,2-propylene glycol/water and the solution is then filtered sterile.

EXAMPLE 3

Lotion 100 g of lotion contains:

| Gallidermin | 1.00 g |
|---|---|
| 1,2-Propylene glycol | 7.00 g |
| Alkyldimethylbenzylammonium chloride (Benzalkon A ®) | 0.15 g |
| Sorbitan monopalmitate (Span 40 ®) | 0.40 g |
| Sorbimacrogol palmitate (Tween 40 ®) | 1.20 g |
| Decyl Oleate (Cetiol V ®) | 2.40 g |
| Mixture of cetyl and stearyl alcohols (Lanette O ®) | 1.60 g |
| Cetly palmitate | 0.80 g |
| Demineralized water ad | 100 g |

Preparation

The above quantities of alkyldimethylbenzylammonium chloride, sorbitan monopalmitate, sorbimacrogol palmitate, decyl oleate, cetyl and stearyl alcohols and cetyl palmitate are stirred into 75 ml of water, the filtered solution of gallidermin in 1,2-propylene glycol and the remaining water are stirred in, and the tincture is homogenized.

EXAMPLE 4

Gel 100 g of gel contains:

| Gallidermin | 1.0 g |
|---|---|
| Polyethylene glycol ether of lauryl alcohol (Brij 35 ®) | 1.0 g |
| 1,2-Propylene glycol | 5.0 g |
| Acrylic acid polymer (Carbopol 934 ®) | 1.2 g |
| Methyl p-hydroxybenzoate | 1.6 g |
| Propyl p-hydroxybenzoate | 0.4 g |
| Perfume | q.s |
| Sodium hydroxide solution ad | pH 6.5 |
| Demineralized water ad | 100 g |

Preparation

The specified quantities of excipient are stirred into 75 ml of water; the gallidermin is dissolved in a mixture of 1,2-propylene glycol and the remaining water, and this solution is again stirred in; the finished gel is homogenized once more.

Reference Example 1

When subjected to thin layer chromatography on silica gel plates 60F$_{254}$ (Merck Darmstadt), the following R$_f$ values were found for gallidermin:

| R$_f$(chloroform/methanol/17% NH$_3$ 2:2:1) | = 0.73 |
|---|---|
| R$_f$(chloroform/methanol/17% NH$_3$ 70:35:10) | = 0.30 |
| R$_f$(1-buanol/acetic acid/water 4:1:1) | = 0.05 |

Reference Example 2

Total hydrolysis of the peptide (100 nmol) was carried out in 6N HCl (200 μl) containing thioglycolic acid (5 μl) under nitrogen at 110° C. for 18 hours in sealed vials. After evaporation the residual hydrolysate was dissolved in sodium citrate buffer pH 2.2 and analysed using the standard program of the amino acid analyzer LKB 4150. The following values were found (calc.):

Ala 1.98 (2), Asp 0.98 (1), Gly 2.10 (2), Ile 0.92 (1), Leu 0.98 (1), Lan 2.0 (2), Lys 1.91 (2), MeLan 1.0 (1), Phe 1.86 (2), Pro 0.91 (1), Tyr 0.87 (1).

Reference Example 3

Determination of the configuration of the amino acids

The configuration of the protein amino acids and in particular of lanthionine and 3-methyllanthionine was determined according to a recently elaborated gas-chromatographic method (Kusters E. et al. Chromatographia 18, 287–293 (1984)) separating trifluroacetylated amino acid n-propyl esters on glass capillaries (25–33 m) coated with Chirasil-Val (Frank H. et al., J. Chromatographia, 146, 197–206 (1978)) using a gas chromatograph Sichromat Autoderivat 100 (Siemens). Samples containing approximately 100 nmol of amino acids were derivatized as follows: esterification with 4N HCl/1-propanol (1 ml) at 110° C. for 30 minutes in a sealed vial; after drying in a stream of nitrogen trifluoroacetic anhydride (50 µl) was added and heated in the sealed vial at 140° C. for 10 minutes. Again the solution was evaporated in a stream of nitrogen. For analysis samples were applied in dichloromethane. The carrier gas was nitrogen and a flame ionization detector was use. For the temperature program see the above mentioned references. The following values were found:

L-Ala(2), L-Asp (1), L-Gly (2), L-Ile (1), meso-Lan (2), L-Leu (1), L-Lys (2), (2S, 3S, 6R)-3-Melan (1), L-Phe (2), L-Pro (1).

Reference Example 4

Tryptic cleavage

Gallidermin was dissolved in a buffer solution (1 mg/ml) consisting of 0.05M N-ethylmorpholine acetate, 0.01M $CaCl_2.6H_2O$, pH 7.8 and trypsin (50 µg Calbiochem). After 24 hours at 37° C. the enzymic cleavage was stopped by addition of acetic acid to pH 4, and the solution was cooled to 0° C. in order to precipitate the C-terminal fragment 14–21. After centrifugation the supernatant was lyophilized and the soluble components were purified by RP-HPLC to yield the N-terminal fragment 1–13.

Reference Example 5

Mass spectrometry

Figure 3:
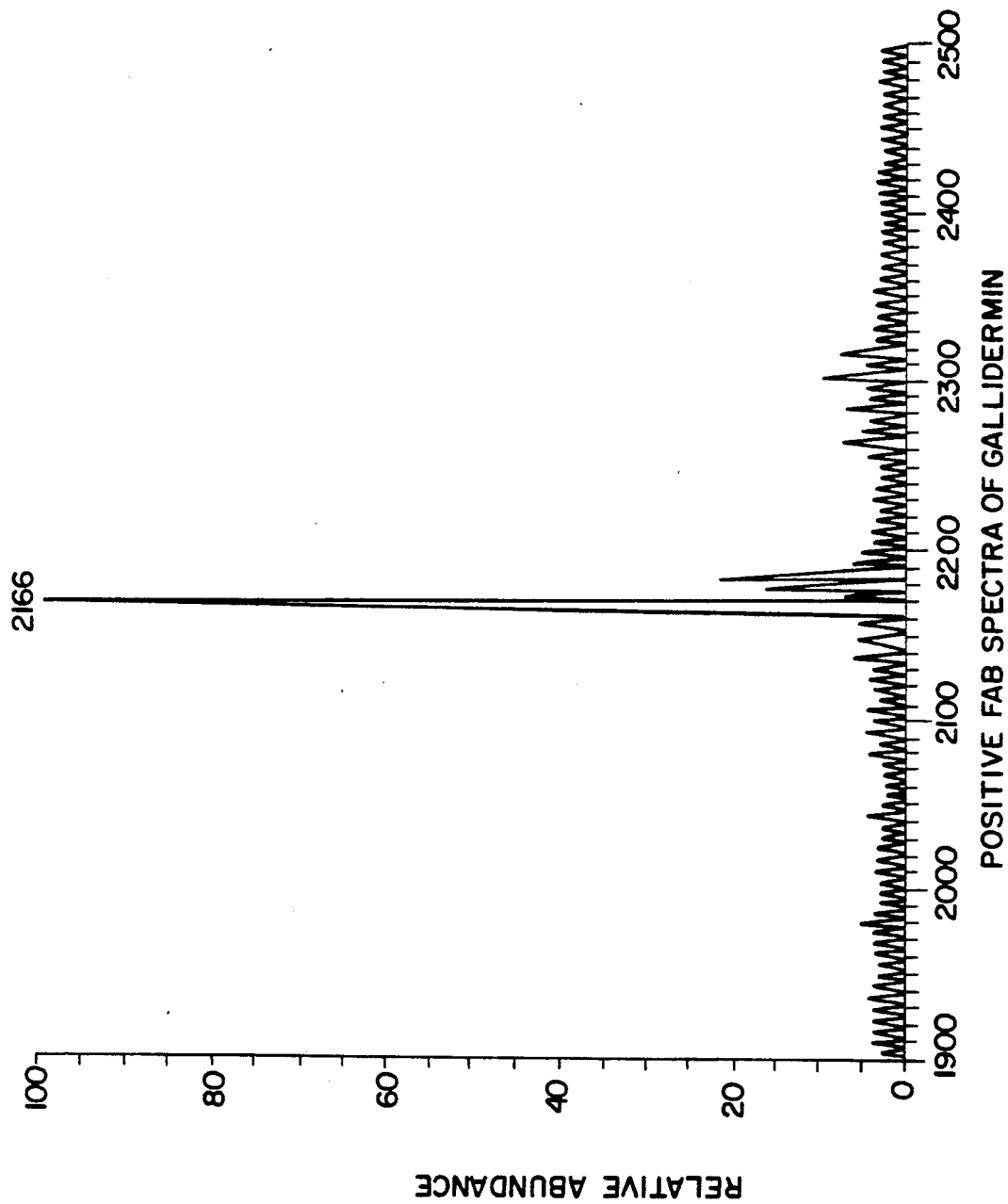
FIG. 3 shows the positive FAB mass spectra of gallidermin.

Positive FAB mass spectra (FIG. 3) were recorded with a spectrometer VG 70/250/SEQ equipped with a cesium ion source. Samples were applied in 3-nitrobenzyl-alcohol/methanol matrix.

Figure 3B:
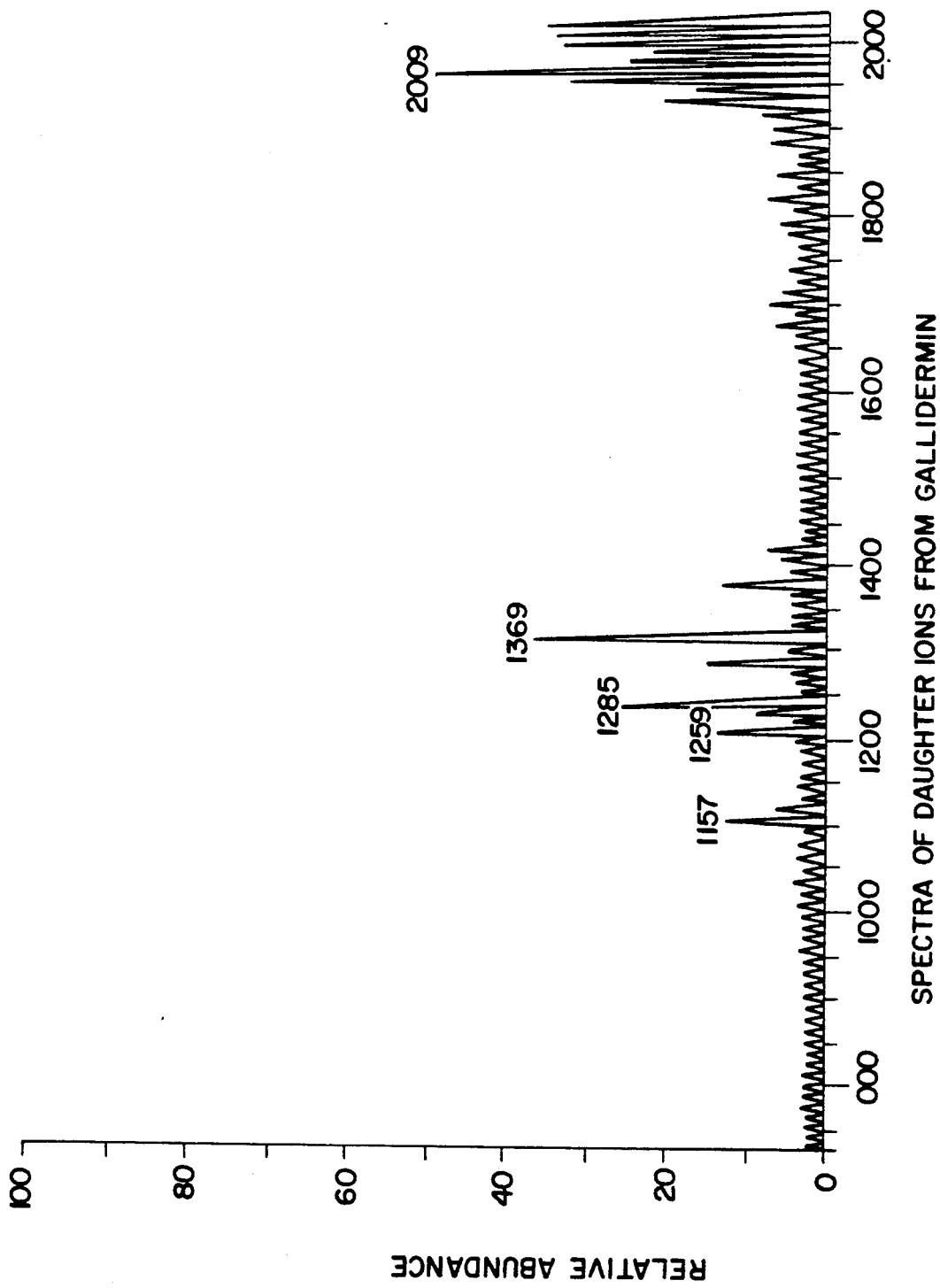
FIG. 3B shows the spectra of daughter ions from gallidermin.

The value $[M+H]^+$: 2166 M.U. confirmed the calculated molecular mass. The spectrum of the daughter ions (FIG. 3b) shows the fragments $B_{12}$, $B_{13}$, $B_{14}$ and $B_{15}$. These fragments are typical for the tryptic cleavage site and this overlap combines the results obtained for the N- and C-terminal fragments analysed separately.

Thermospray ionization mass spectra were obtained using the thermospray system HP 5988 (Hewlett Packard). Samples of the tryptic fragment 14–21 of gallidermin were injected. Positive ionization with additional electron impact was applied and the ions were detected in the scan region of 350–950 mass unites. In the significant region of 350–550 mass units detection of several fragments was obtained after background subtraction and confirmed via coelution of masses.

Figure 2:
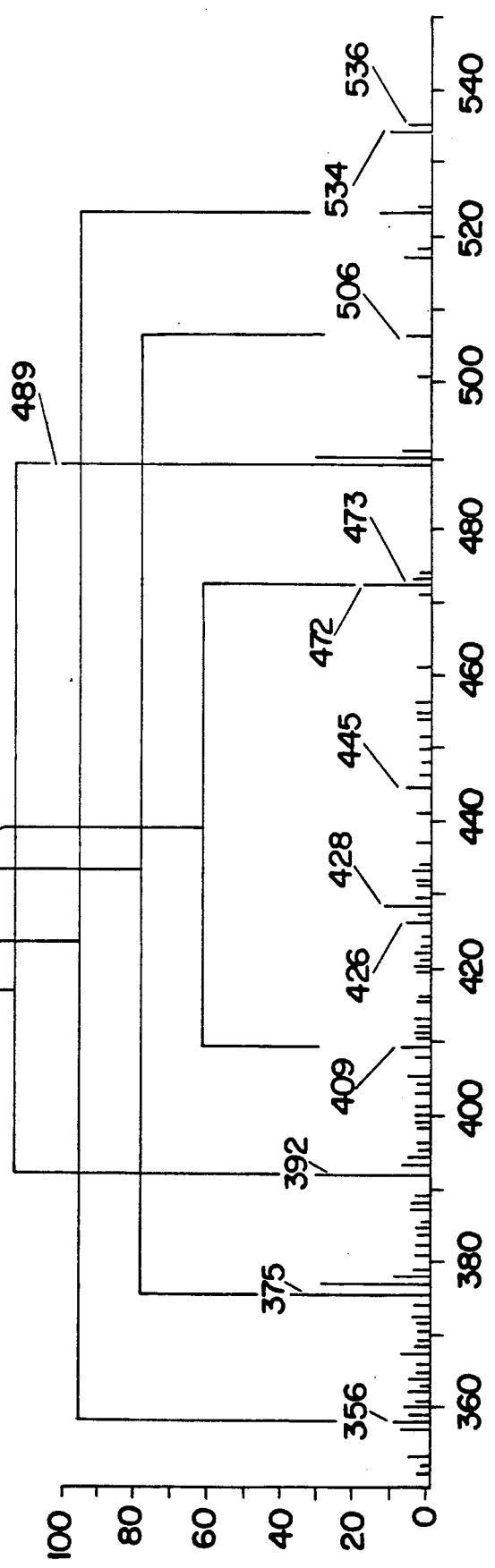
FIG. 2 shows the thermospray ionization mass spectra of gallidermin in the scan region 350-550 daltons.

The spectrum is shown in the scan region 350–550 daltons in FIG. 2. The stability of Cys(Avi) which forms the amidated C-terminus is noteworthy because it forms the main peak. A characteristic fourfold fragmentation each with twofold bond cleavage is characteristic for both C-terminal fragments Gallidermin 14–21 and epidermin 14–21. Coelution of the masses confirms this peculiar fragmentation pattern.

Reference Example 6

Peptide sequencing

Gallidermin and its N-terminal fragment were sequenced by automated Edman degradation using a pulsed-liquid gas phase sequencer 477A with on-line PTH-analyser (Applied Biosystems). Samples of RP-HPLC separations dissolved in the HPLC eluant were applied directly to the filter disc in the reaction chamber.

Sequencing and PTH analysis wee carried out with the standard program.

This analysis revealed the N-terminal sequence $Ile^1$-$Ala^2$-$x^3$-$Lys^4$-$Phe^5$-$Leu^6$-$x^7$-$x^8$-$Pro^9$-$Gly^{10}$-$x^{11}$-$Ala^{12}$-$Lys^{13}$.

The x at position 3, 7 8 and 11 designate the positions in which no amino acid derivative was detected. These positions correspond to one Lan and one MeLan residue according to the amino acid composition of the N-terminal fragment.

Figure 4:
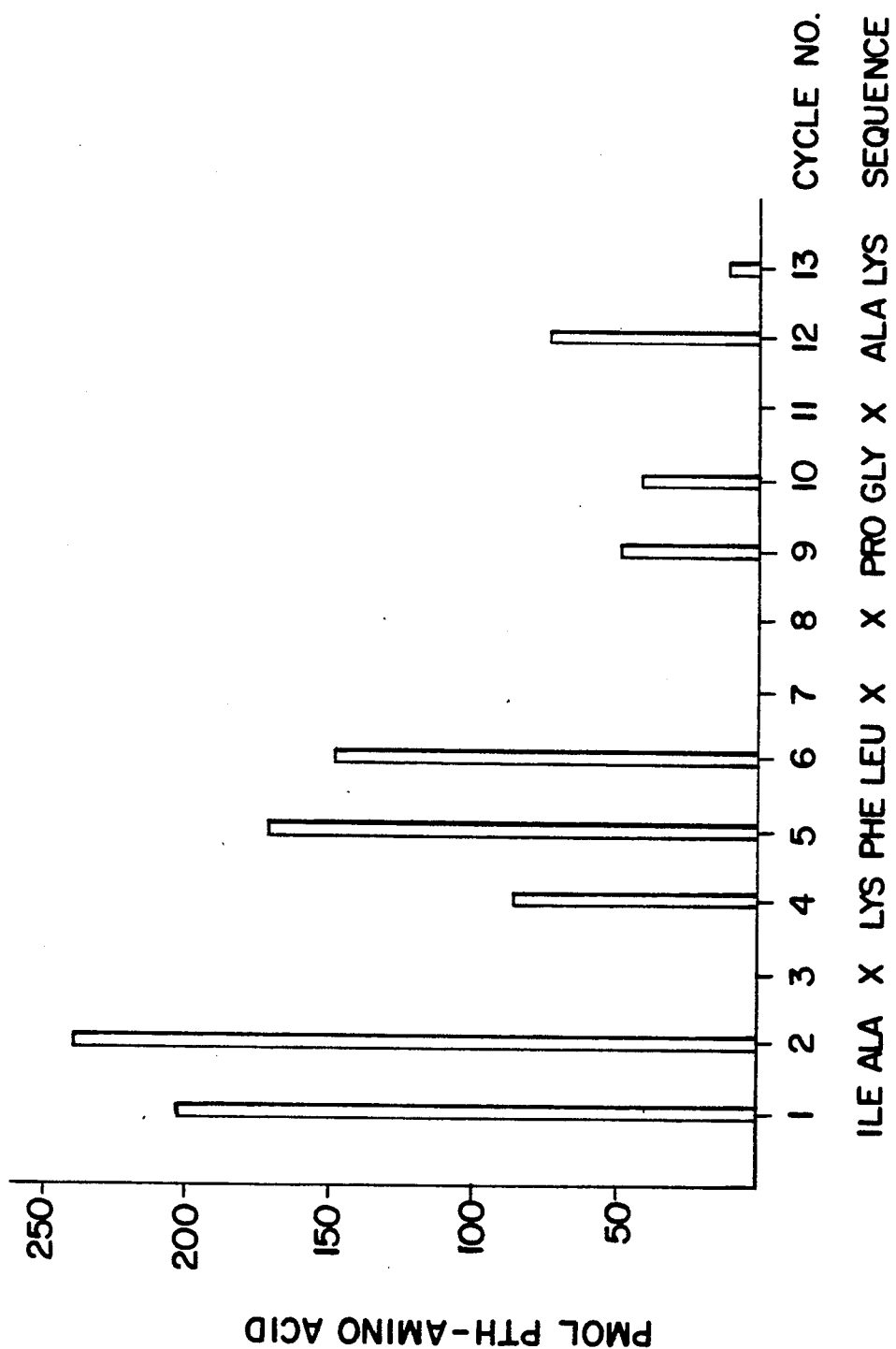
FIG. 4 shows degradation yields for gallidermin in peptide sequencing.

Because of the sulfide bridges and the peculiar properties of the bis-PTH-Lan automatic degradation cannot be evaluated at these positions, however degradation proceeds further. The degradation yields for gallidermin are shown in FIG. 4.

The amino acid Leu was detected unequivocally in position 6.

There is a characteristic enzymic cleavage site $Lys^{13}$-$Dhb^{14}$ in the central part of gallidermin. During tryptic digestion precipitation of the resulting C-terminal noncharged and hydrophobic fragment 14–21 is observed, whereas the N-terminal fourfold charged and hydrophilic fragment 1–13 remains in solution.

The cleavage rate for the Lys-Dhb bond is very slow compared to other bonds of Lys with any protein amino acid. As in the case of epidermin tryptic cleavage leads to the conversion of Dhb to 2-oxobutyryl residue which prevents structure elucidation by Edman degradation of the C-terminal fragment.

Reference Example 7

Ultra-violet analysis

The UV spectrum of gallidermin confirms the vinylic double bond at 267 nm which exhibits the very high extinction coefficient of 11000 $M^{-1}cm^{-1}$ (water, 0.1 mg/ml, d=2 cm, 21° C.) compared to the low value of the tyrosine absorption (1400 $M^{-1}cm^{-1}$).

What is claimed is:

1. A method for producing gallidermin, having the formula

H—Ile—Ala—

```
       CH2——————— S ———————CH2
        |                   |
  —NH—CH—CO—Lys—Phe—Leu—NH—CH—CO—NH—
      —D—                   —L—
```

-continued

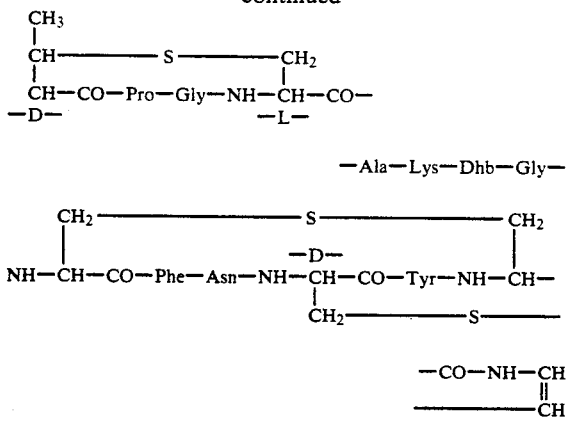

comprising the steps of cultivating *Staphylococcus gallinarum*, having an accession number DSM 4616, in a suitable medium comprising a nitrogen source, a carbon source and an hydroxide of an alkaline earth metal under aeration and in a pH range of about 5.4 to about 8.5 and isolating the gallidermin from the medium.

2. The method of claim 1 further characterized in that gallidermin is isolated by treating the culture medium with an adsorber in order to adsorb the gallidermin therein, eluting the adsorbed gallidermin from the adsorber, subjecting the eluate to chromatographic separation using a weak cation exchange resin and desalting the gallidermin-containing eluate.

3. The method of claim 2 further characterized in that the desalted gallidermin-containing eluate is then further purified by reverse-phase HPLC and gel chromatography.

* * * * *